United States Patent
Nakajima et al.

(10) Patent No.: US 11,312,831 B2
(45) Date of Patent: Apr. 26, 2022

(54) CARRIER FOR BIO-RELATED MOLECULE IMMOBILIZATION

(71) Applicant: TOYO SEIKAN GROUP HOLDINGS, LTD., Tokyo (JP)

(72) Inventors: Kazuki Nakajima, Yokohama (JP); Shinya Jumyo, Yokohama (JP); Yoshihiro Saruwatari, Tokyo (JP); Norio Akuzawa, Yokohama (JP); Ken Kashiwabara, Yokohama (JP)

(73) Assignee: Toyo Seikan Group Holdings, Ltd., Tokyo (JP)

( * ) Notice: Subject to any disclaimer, the term of this patent is extended or adjusted under 35 U.S.C. 154(b) by 115 days.

(21) Appl. No.: 16/347,600

(22) PCT Filed: Nov. 20, 2017

(86) PCT No.: PCT/JP2017/041694
§ 371 (c)(1),
(2) Date: May 6, 2019

(87) PCT Pub. No.: WO2018/092908
PCT Pub. Date: May 24, 2018

(65) Prior Publication Data
US 2019/0276598 A1 Sep. 12, 2019

(30) Foreign Application Priority Data

Nov. 18, 2016 (JP) .............................. JP2016-225289
Dec. 20, 2016 (JP) .............................. JP2016-246377

(51) Int. Cl.
| | | |
|---|---|---|
| *C08G 64/16* | (2006.01) | |
| *C08K 5/544* | (2006.01) | |
| *G01N 33/543* | (2006.01) | |
| *C08K 3/04* | (2006.01) | |
| *C08J 7/06* | (2006.01) | |
| *G01N 33/53* | (2006.01) | |
| *C12N 15/09* | (2006.01) | |
| *G01N 37/00* | (2006.01) | |
| *C12M 1/00* | (2006.01) | |
| *C08J 7/056* | (2020.01) | |
| *C12Q 1/6837* | (2018.01) | |

(52) U.S. Cl.
CPC ............ *C08J 7/06* (2013.01); *C08G 64/1608* (2013.01); *C08J 7/056* (2020.01); *C08K 3/04* (2013.01); *C12M 1/00* (2013.01); *C12N 15/09* (2013.01); *G01N 33/53* (2013.01); *G01N 33/543* (2013.01); *G01N 37/00* (2013.01); *C12Q 1/6837* (2013.01)

(58) Field of Classification Search
CPC ......... C08G 64/1608; C08J 7/056; C08J 7/06; C08K 3/04; C08K 5/544; C12M 1/00; C12N 15/09; C12Q 1/6837; G01N 33/53; G01N 33/543; G01N 37/00
See application file for complete search history.

(56) References Cited

U.S. PATENT DOCUMENTS

| | | |
|---|---|---|
| 6,464,848 B1 | 10/2002 | Matsumoto |
| 9,050,577 B2 * | 6/2015 | Yamano ............... B01J 19/0046 |
| 2005/0176003 A1 | 8/2005 | Yokoyama et al. |
| 2006/0204959 A1 | 9/2006 | Okamura et al. |
| 2009/0098301 A1 | 4/2009 | Okamura et al. |
| 2009/0111113 A1 | 4/2009 | Okamura et al. |
| 2012/0171503 A1 | 7/2012 | Yamano |

FOREIGN PATENT DOCUMENTS

| | | |
|---|---|---|
| JP | 2001-108683 A | 4/2001 |
| JP | 3214562 B2 | 10/2001 |
| JP | 2003-161731 A | 6/2003 |
| JP | 2005-043312 A | 2/2005 |
| JP | 4370874 A | 5/2005 |
| JP | 2005-201901 A | 7/2005 |
| JP | 2008/249416 A | 10/2008 |

(Continued)

OTHER PUBLICATIONS

International Preliminary Report on Patentability issued for PCT/JP2017/041694 dated May 21, 2019.*
Howarter et al., "Surface Modification of Polymers with 3-Aminopropyltriethoxysilane as a General Pretreatment for Controlled Wettability," Macromolecules, 2007, vol. 40, No. 4, pp. 1128-1132.*
Machine translation of JP 2005-043312 A, published Feb. 17, 2005.*
Machine translation of JP 2008-249416 A, published Oct. 16, 2008.*
Jang et al., "Polycarbonate Bonding Assisted by Surface Chemical Modification Without Plasma Treatient and its Application for the Construction of Plastic-based Cell Arrays", Sensors and Actuators A, vol. 206, 2014, pp. 57-66.

(Continued)

*Primary Examiner* — Galina M. Yakovleva
(74) *Attorney, Agent, or Firm* — Marshall, Gerstein & Borun LLP

(57) ABSTRACT

The present invention relates to a carrier for bio-related molecule immobilization, which comprises a resin substrate, an amino group-containing compound layer that is formed on the resin substrate, and a polyvalent carboxylic acid layer that is formed on the amino group-containing compound layer. The carboxyl groups in the polyvalent carboxylic acid layer are actively esterified; and the (COO peak intensity)/(C—C peak intensity) ratio of the C1s spectrum is from 0.064 to 0.12 (inclusive) if the carrier surface before the active esterification is measured by X-ray photoelectron spectroscopy. The present invention also relates to a carrier for bio-related molecule immobilization, which comprises a water repellent resin substrate, an aminoalkyl silane layer that is formed on the resin substrate and a polyvalent carboxylic acid layer that is formed on the aminoalkyl silane layer, and which is characterized in that: the carboxyl groups in the polyvalent carboxylic acid layer are actively esterified; and the resin substrate is exposed after the formation of the aminoalkyl silane layer.

5 Claims, 4 Drawing Sheets

(56) References Cited

FOREIGN PATENT DOCUMENTS

| JP | 2010-060291 A | 3/2010 |
|----|---------------|--------|
| JP | 2011-516885 A | 5/2011 |
| JP | 4764901 B2 | 9/2011 |
| JP | 5735426 B2 | 6/2015 |
| WO | WO-03/046562 A1 | 6/2003 |
| WO | WO-2011/030823 A1 | 3/2011 |

OTHER PUBLICATIONS

Search Report and Written Opinion in International Application No. PCT/JP2017/041694 dated Feb. 13, 2018, 8 pages.
Extended European Search Report in EP Application No. 17872112.2 dated Apr. 7, 2020, 7 pages.

* cited by examiner

EXPERIMENTAL EXAMPLE 2-1

EXPERIMENTAL EXAMPLE 2-10

EXPERIMENTAL EXAMPLE 2-16

EXPERIMENTAL EXAMPLE 2-1

EXPERIMENTAL EXAMPLE 2-10

EXPERIMENTAL EXAMPLE 2-16

EXPERIMENTAL EXAMPLE 2-11

EXPERIMENTAL EXAMPLE 2-12

EXPERIMENTAL EXAMPLE 2-13

EXPERIMENTAL EXAMPLE 2-14

EXPERIMENTAL EXAMPLE 2-15

CARRIER FOR BIO-RELATED MOLECULE IMMOBILIZATION

TECHNICAL FIELD

The present invention relates to a carrier for bio-related molecule immobilization, and a method of producing the same.

BACKGROUND ART

With a demand for safety and soundness of environments and foods, development of techniques for controlling microbial contamination in environmental samples, food ingredients, or products is in progress. As a means for achieving these objects, a method of detecting bio-related molecules such as nucleic acids derived from microorganisms is advantageous in terms of detection sensitivity, specificity, and the like, and development has been carried out for various carriers such as microarrays and DNA chips, in which bio-related molecules are immobilized on a surface-treated substrate. In these carriers, precise spotting apparatuses are used to spot multiple solutions containing different bio-related molecules individually on the substrate in small spots.

Carriers for immobilizing bio-related molecules as described above include a carrier which has a polyvalent amine layer on a substrate prepared from various materials and which further has an active ester group thereon (Japanese Patent No. 4764901 and Japanese Patent Application Publication No. 2003-161731), a carrier which has an electrostatic layer on a substrate and which further has an active ester group thereon in the same manner (Japanese Patent No. 5735426), and a carrier which has an aminoalkylsilane and an active ester group on a substrate in the same manner (Japanese Patent No. 4370874). There are many known types and methods for surface treatment of substrates. However, the performance of spotting and detecting bio-related molecules may be greatly affected depending on the specific types and application conditions for various substrates and surface treatment. Therefore, there is need for further technical development.

SUMMARY OF INVENTION

The surface treatment of a substrate for immobilizing bio-related molecules has a problem that, for example, a substrate using a polyvalent carboxylic acid such as polyacrylic acid has a high surface wettability, so that the spot diameter of a solution containing bio-related molecules becomes large when the solution is spotted on the substrate. Besides, in the present technical field, improvement in detection sensitivity (S/N ratio) is always a demand. As described above, there is a need for developing a technique which makes it possible to further increase the detection sensitivity of bio-related molecules while keeping the spot diameter small so as to prevent the bio-related molecule solution from spreading.

The inventors of the present invention have found that the above problems can be solved by preparing a carrier for bio-related molecule immobilization which includes a resin substrate and has an amino group-containing compound layer and a polyvalent carboxylic acid layer stacked in this order on the substrate, in which a ratio (COO peak intensity)/(C—C peak intensity) of a C1s spectrum as measured on a carrier surface after the stacking by X-ray photoelectron spectroscopy is in a predetermined range.

Specifically, in a first aspect, the present invention provides a carrier for bio-related molecule immobilization comprising: a resin substrate; an amino group-containing compound layer formed on the resin substrate; and a polyvalent carboxylic acid layer formed on the amino group-containing compound layer, wherein a carboxyl group of the polyvalent carboxylic acid layer is subjected to active esterification, and wherein a ratio (COO peak intensity)/(C—C peak intensity) of a C1s spectrum as measured on a carrier surface before the active esterification by X-ray photoelectron spectroscopy is 0.064 or more and 0.12 or less.

In addition, the first aspect of the present invention provides a method of producing a carrier for bio-related molecule immobilization, the method comprising: forming an amino group-containing compound layer on a resin substrate; forming a polyvalent carboxylic acid layer on the amino group-containing compound layer; and subjecting a carboxyl group of the polyvalent carboxylic acid layer to active esterification, wherein the steps of forming an amino group-containing compound layer and the step of forming a polyvalent carboxylic acid layer are conducted under a condition that a ratio (COO peak intensity)/(C—C peak intensity) of a C1s spectrum as measured on a carrier surface after the formation of the polyvalent carboxylic acid layer by X-ray photoelectron spectroscopy is 0.064 or more and 0.12 or less.

In the first aspect of the present invention, it is possible to obtain a carrier with high detection sensitivity while keeping small the spot diameter at the time of spotting a solution containing bio-related molecules if the carrier for bio-related molecule immobilization is prepared by using a resin substrate, subjecting the substrate to surface treatment to form a polyvalent carboxylic acid layer, and controlling a measured value of a C1s spectrum as measured on a carrier surface by X-ray photoelectron spectroscopy.

In addition, as described above, there are many known methods and types of surface treatment of a substrate for immobilizing bio-related molecules, and as one representative example for amino group-containing compounds, aminoalkylsilanes are widely known. However, a substrate which is subjected to aminoalkylsilane treatment and then is allowed to adsorb a polyvalent carboxylic acid such as polyacrylic acid has a problem that, when a solution containing bio-related molecules is spotted on the surface thereof, the spot diameter becomes large or the spot shape becomes poor. In particular, in general, it is common to improve the efficiency of forming an aminoalkylsilane layer by hydrophilization of the substrate for the purpose of sufficient surface treatment. However, a carrier prepared in this manner is inferior in spot shape for a nucleic acid solution, and thus there is a need for developing a technique which makes it possible to keep the spot diameter small so as to prevent the nucleic acid solution from spreading.

The inventors of the present invention have found that the above problems can be solved by preparing a carrier which includes a resin substrate and has an aminoalkylsilane layer and a polyvalent carboxylic acid layer stacked in this order on the substrate, in which a water repellent resin substrate is used and the amount of aminoalkylsilane introduced is controlled so as to expose the resin substrate in the formation of an aminoalkylsilane layer by surface treatment of the substrate.

Specifically, in a second aspect, the present invention provides a carrier for bio-related molecule immobilization comprising: a water repellent resin substrate; an aminoalkylsilane layer formed on the resin substrate; and a polyvalent carboxylic acid layer formed on the aminoalkylsilane layer, wherein a carboxyl group of the polyvalent carboxylic acid layer is subjected to active esterification, and wherein the resin substrate is exposed after the formation of the aminoalkylsilane layer.

In addition, the second aspect of the present invention provides a method of producing a carrier for bio-related molecule immobilization, the method comprising: forming an aminoalkylsilane layer on a water repellent resin substrate; forming a polyvalent carboxylic acid layer on the aminoalkylsilane layer; and subjecting a carboxyl group of the polyvalent carboxylic acid layer to active esterification, wherein the step of forming an aminoalkylsilane layer is conducted under a condition that the resin substrate is exposed after the formation of the aminoalkylsilane layer.

In the second aspect of the present invention, it is possible to obtain a carrier for bio-related molecule immobilization with a good spot shape by using a water repellent resin substrate and controlling the amount of aminoalkylsilane introduced so as to expose the resin substrate in the formation of an aminoalkylsilane layer by surface treatment of the substrate.

DESCRIPTION OF EMBODIMENTS

Figure 1:
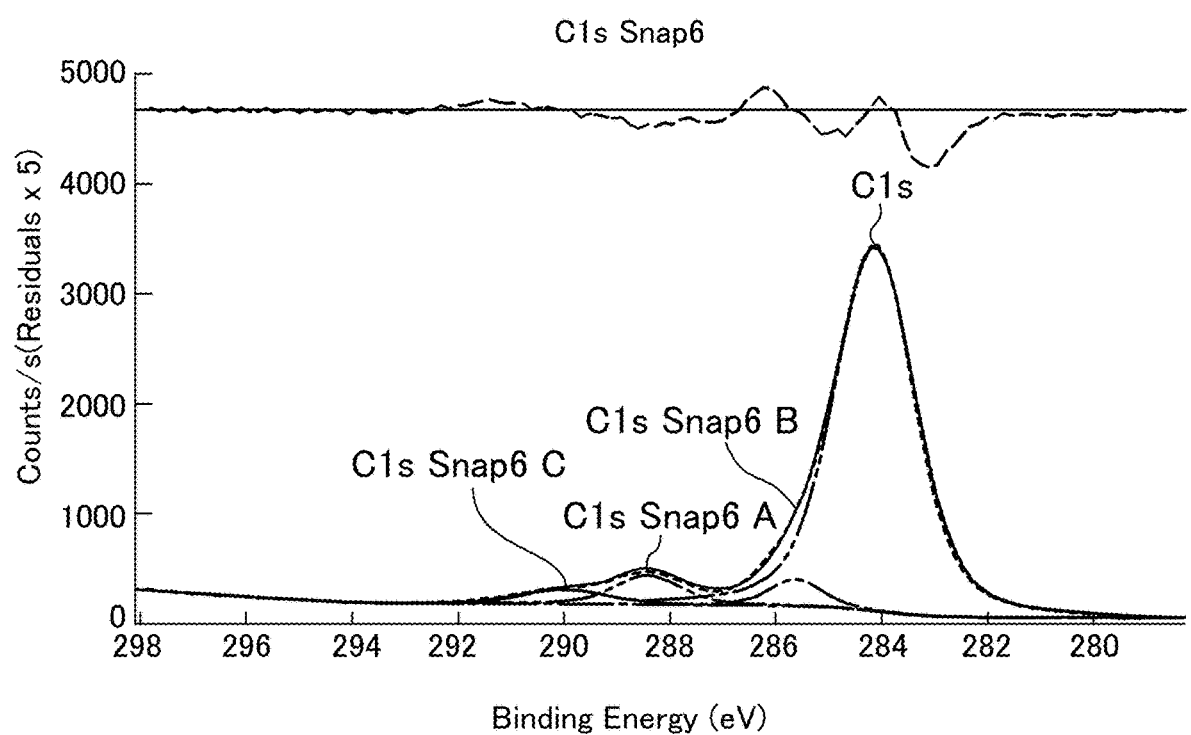
FIG. 1 illustrates a C1s spectrum of XPS surface analysis on a substrate after polyacrylic acid treatment of Example 1-4. The peak detected in the vicinity of 288.4 eV is the C—C peak considered to be mainly derived from the resin substrate, and the peak detected in the vicinity of 284.7 eV is the COO peak considered to be derived from the carboxyl groups of the polyvalent carboxylic acid layer.

1. A first aspect of the present invention provides a carrier for bio-related molecule immobilization comprising: a resin substrate; an amino group-containing compound layer formed on the resin substrate; and a polyvalent carboxylic acid layer formed on the amino group-containing compound layer, wherein a carboxyl group of the polyvalent carboxylic acid layer is subjected to active esterification, and wherein a ratio (COO peak intensity)/(C—C peak intensity) of a C1s spectrum as measured on a carrier surface before the active esterification by X-ray photoelectron spectroscopy is 0.064 or more and 0.12 or less.

The first aspect of the present invention uses a resin substrate. Although the type of resin is not particularly limited, it is preferable to use a material having as low autofluorescence as possible because the detection of bio-related molecules such as nucleic acids is often carried out based on fluorescent substances bound to the bio-related molecules. Specifically, the types of resin include polyethylene, polypropylene, cyclic polyolefin, polyisobutylene, polyethylene terephthalate, unsaturated polyester, fluorine-containing resins, polyvinyl chloride, polyvinylidene chloride, polyvinyl acetate, polyvinyl alcohol, polyvinyl acetal, acrylic resins, polyacrylonitrile, polystyrene, acetal resins, polycarbonate, polyamide, phenolic resins, urea-formaldehyde resins, epoxy resins, melamine resins, styrene-acrylonitrile copolymer, acrylonitrile-butadiene styrene copolymer, and organic materials such as polyphenylene oxide and polysulfone, and a mixture resin of two or more kinds from these may be used. In addition, additional substances capable of improving the performance according to the desired purpose, such as improvement of detection sensitivity, may be added as appropriate, and a black pigment such as a carbon black may be mixed, for example.

In the first aspect of the present invention, as the material for the resin substrate, it is preferable to use a polycarbonate and more preferable to use a polycarbonate containing a carbon black as a black pigment. The amount of the carbon black can be determined as appropriate by those skilled in the art, and the material used is one containing a carbon black in the resin in an amount of, for example, 0.1% by weight to 2% by weight, preferably 0.2% by weight to 1% by weight, and more preferably 0.3% by weight to 0.8% by weight.

In the carrier for bio-related molecule immobilization of the first aspect of the present invention, an amino group-containing compound layer is formed on the resin substrate described above. As the amino group-containing compound contained in the amino group-containing compound layer, it is possible to use any compound having one or more unsubstituted or substituted amino groups, and it is possible to use compounds containing ammonia, various amines, amino alcohols, aminoalkylsilanes, and the like, for example. The above amines include allylamine, monomethylamine, dimethylamine, monoethylamine, diethylamine, ethylenediamine, hexamethylenediamine, and n-propylamine. Among the above, the first aspect of the present invention preferably uses an aminoalkylsilane as the amino group-containing compound. For example, the aminoalkylsilane used is one whose alkyl group has 1 to 10 carbon atoms and preferably 2 to 5 carbon atoms, and specifically, the alkyl group can include methyl groups, ethyl groups, propyl groups, butyl groups, and pentyl groups. Among the above, a propyl group is particularly preferable in the first aspect of the present invention. In addition, the silane of the aminoalkylsilane may be substituted with one or more substituents. For example, it is possible to use one substituted with an alkoxy group (such as a methoxy group, an ethoxy group, a propoxy group, or a butoxy group) having 1 to 5 and preferably 2 to 4 carbon atoms. It is particularly preferable that the silane be substituted with three ethoxy groups. Specifically, the aminoalkylsilane includes 3-aminopropyltriethoxysilane, 3-aminopropyltrimethoxysilane, 3-aminopropyldiethoxymethylsilane, and 3-aminopropyldimethoxyethylsilane. In the first aspect of the present invention, 3-aminopropyltriethoxysilane is particularly preferable. Note that the amino group-containing compound layer may be formed on at least part of the surface of the substrate, and does not need to cover the entire surface of the substrate.

No particular limitation is imposed on the method of forming an amino group-containing compound layer. For example, it is possible to form an amino group-containing compound layer by immersing the substrate in a solution prepared by dissolving the above-described amino group-containing compound in various solvents. The types of solvent used can include alcohols such as methanol and ethanol. For the purpose of reducing the surface roughness of the substrate to suppress autofluorescence, it is preferable to use water as the solvent and immerse the substrate in an aqueous solution in which the amino group-containing compound is sufficiently hydrolyzed.

The immersion time and the concentration of the solution of the amino group-containing compound can be set as appropriate by those skilled in the art in consideration of the type of the specific compound used so as to obtain a predetermined peak intensity ratio of the present invention to be described later. For example, it is possible to use a solution of 1% by weight to 10% by weight and preferably 3% by weight to 8% by weight, and it is possible to set the immersion time to 15 minutes to 180 minutes and preferably 30 minutes to 120 minutes.

In the carrier for bio-related molecule immobilization of the first aspect of the present invention, a polyvalent carboxylic acid layer is further formed on the amino group-containing compound layer described above. When the polyvalent carboxylic acid layer is formed in this manner, carboxyl groups are introduced to the surface side of the carrier. No particular limitation is imposed on the type of the polyvalent carboxylic acid used in the first aspect of the present invention. For example, it is possible to use a homopolymer or a copolymer of a monomer having a carboxyl group such as polyacrylic acid, polymethacrylic acid, polymaleic acid, polyitaconic acid, and acrylic acid-methacrylic acid copolymers. When the carboxyl group of the polyvalent carboxylic acid forms an amide bond with the amino group of the amino group-containing compound layer, the polyvalent carboxylic acid layer can be firmly bound on the amino group-containing compound layer. Note that the polyvalent carboxylic acid layer may be formed on at least part of the surface of the underlying substrate and/or the amino group-containing compound layer, and does not need to cover the entire surface of the substrate and/or the amino group-containing compound layer.

No particular limitation is imposed on the method of forming a polyvalent carboxylic acid layer. The method includes a method of immersing the substrate having an amino group-containing compound layer formed thereon in a solution of the polyvalent carboxylic acid. The solvent used for the solution of the polyvalent carboxylic acid can be selected as appropriate by those skilled in the art, and it is possible to use water and various types of organic solvents including alcohols such as methanol and ethanol. In the first aspect of the present invention, it is preferable to use an aqueous solution.

The immersion time, the concentration, and the molecular weight of the solution of the polyvalent carboxylic acid layer can be set as appropriate by those skilled in the art in consideration of the type of the specific polyvalent carboxylic acid so as to obtain a predetermined peak intensity ratio of the present invention to be described later. For example, the molecular weight selected is 25,000 to 1,000,000, preferably 50,000 to 500,000, and particularly preferably 100,000 to 200,000, the concentration selected is 0.1% by weight to 10% by weight, preferably 0.5% by weight to 10% by weight, and particularly preferably 1.0% by weight to 5.0% by weight, and the immersion time selected is 1 minutes to 60 minutes, preferably 5 minutes to 30 minutes, and particularly preferably 10 minutes to 20 minutes.

As described above, as regards the carrier which includes a resin substrate and has an amino group-containing compound layer and further a polyvalent carboxylic acid layer stacked on the substrate, a ratio (COO peak intensity)/(C—C peak intensity) (hereinafter simply referred to as the "peak intensity ratio" as well) of a C1s spectrum as measured on the surface of the carrier by X-ray photoelectron spectroscopy is 0.064 or more and 0.12 or less. The above peak intensity ratio is preferably 0.064 or more and 0.10 or less, further preferably 0.064 or more and less than 0.10, and particularly preferably 0.070 or more and 0.094 or less. Alternatively, the above peak intensity may be in a range of 0.10 or more and 0.12 or less. When the carrier for bio-related molecule immobilization is prepared such that the peak intensity ratio after the formation of the polyvalent carboxylic acid layer is in the above-described range, it is possible to obtain a DNA chip with high detection sensitivity while keeping small the spot diameter at the time of spotting a solution containing bio-related molecules.

Note that the "COO peak intensity" described above means the intensity of the peak derived from the carboxyl groups on the substrate surface measured by C1s spectrum, and represents the measured value for the peak observed in the vicinity of a binding energy of 288.4 eV. In addition, the "C—C peak intensity" described above means the intensity of the peak derived from the hydrocarbon groups on the substrate surface measured by C1s spectrum, and represents the measured value for the peak observed in the vicinity of a binding energy of 284.7 eV.

The above COO peak is considered to be mainly derived from the carboxyl groups of the polyvalent carboxylic acid layer formed on the uppermost layer of the carrier. For this reason, in general, it is possible to adjust the above peak intensity by adjusting the variational factors capable of controlling the formation of the polyvalent carboxylic acid layer. For example, it is possible to adjust the peak intensity ratio by adjusting the concentration of the solution of the polyvalent carboxylic acid used in the step of forming the polyvalent carboxylic acid layer, the immersion time for immersing the substrate in the solution, and the like. It is apparent that the preferable ranges and specific values of the specific concentration and time can be set when those skilled in the art perform appropriate adjustment based on the actual measured value and the like of the peak intensity. The specific and preferable ranges are as described above.

In addition, the above C—C peak is considered to be mainly derived from the resin substrate, the amino group-containing compound layer, and the polyvalent carboxylic acid layer. In particular, since the resin of the substrate is partially exposed on the surface even after the amino group-containing compound layer and the polyvalent carboxylic acid layer are formed on the resin substrate, the peak intensity is considered to vary depending on the material of the substrate. Therefore, the peak intensity ratio varies depending on the operating conditions (such as the immersion time and the concentration of the solution) in the steps of forming an amino group-containing compound layer and the step of forming a polyvalent carboxylic acid layer, and is a value specific to the material of the substrate.

In the carrier for bio-related molecule immobilization of the first aspect of the present invention, the carboxyl groups of the polyvalent carboxylic acid layer formed as described above are subjected to active esterification. When the carboxyl groups are subjected to active esterification to form active ester groups, it is possible to stably immobilize bio-related molecules when finally spotting a solution of bio-related molecules as a carrier for bio-related molecule immobilization. As regards the type of active ester group and a method of forming the same, there is no particular limitation thereon and those skilled in the art can appropriately select ones suitable for the application as a carrier for bio-related molecule immobilization. The active ester group includes nitrophenyl groups, N-hydroxysuccinimide groups, N-hydroxynorbornene-2,3-dicarboximide groups, succinimide groups, and phthalimide groups. In the first aspect of the present invention, N-hydroxysuccinimide groups are preferable. The method of forming active ester groups includes active esterification of the carboxyl groups of the polyvalent carboxylic acid layer by immersion in a solution prepared by dissolving a dehydration condensation agent such as 1-ethyl- 3-(3-dimethylaminopropyl)carbodiimide hydrochloride and any type of electrophilic group introducing agent corresponding to the active ester group as described above (such as N-hydroxysuccinimide) in a buffer solution.

The carrier for bio-related molecule immobilization of the first aspect of the present invention obtained as described above can immobilize bio-related molecules on its surface. The bio-related molecules in the first aspect of the present invention are preferably nucleic acids. A nucleic acid-containing solution is spotted on a carrier for bio-related molecule immobilization, followed by drying to wash the unreacted nucleic acid solution not bound on the carrier. Thus, it is possible to obtain a carrier with immobilized nucleic acids. The method of spotting a nucleic acid-containing solution on the carrier includes, but is not particularly limited to, a spotting method including bringing a pin holding a nucleic acid-containing solution into contact with the carrier and a method of spraying by ink-jet a nucleic acid-containing solution on the carrier. It is possible to carry out spotting using any apparatus, method, and the like known to those skilled in the art.

The nucleic acid immobilization carrier prepared as described above can be used for detecting the presence of target nucleic acids in the test sample. For example, consider the case of using DNA as a nucleic acid. DNA is extracted from the test sample and amplified, which is hybridized with nucleic acids on a nucleic acid immobilization carrier (such as a DNA chip or a microarray) for detection. This makes it possible to confirm the presence or absence of specific microbial contamination in the test sample. The method of extracting DNA includes the phenol extraction method, the phenol-chloroform extraction method, the alkali dissolution method, and the boiling method. Examples also include a method of extracting DNA using a commercially available DNA extracting reagent or a nucleic acid automatic extraction apparatus.

The target region of the extracted DNA is amplified by a nucleic acid amplification method, if necessary. The target region is a region of chromosomal DNA which can be amplified by the nucleic acid amplification method, and can be set as appropriate depending on the purpose without particular limitation as long as it is possible to detect the detection target microorganism. For example, when the test sample contains cells different in type from the detection target microorganism, the target region preferably has a sequence specific to the detection target microorganism, or may have a sequence common to two or more types of microorganisms depending on the purpose. The nucleic acid amplification method includes the PCR method (polymerase chain reaction), the SDA method (strand displacement amplification), the LCR method (ligase chain reaction), the LAMP method (loop-mediated isothermal amplification), and the ICAN method (isothermal and chimeric primer-initiated amplification of nucleic acids). Among these, it is preferable to use the PCR method. For example, the length of a target region amplified by the PCR method is usually 80 to 1000 bases and preferably 100 to 500 bases.

The amplified DNA is detected with the nucleic acid immobilization carrier of the first aspect of the present invention. The nucleic acids (probes) immobilized on the carrier are detectors which enable detection by binding only to the target bio-related molecules in the case where various bio-related molecules such as specific genes and proteins are coexistent, and it is thus difficult to make a distinguishment from one another and to make a direct selection. For example, consider the case of detecting the nucleic acid of a specific microorganism as a bio-related molecule. The probes used are DNA fragments having a sequence complementary to the base sequence possessed by the nucleic acid of this microorganism, and hybridization with the nucleic acid is carried out. Usually, DNAs of 1 to 200 bases and preferably 10 to 150 bases are immobilized on the probes. Either single stranded or double stranded DNA can be immobilized. In addition, when the target bio-related molecules are labeled with a fluorescent substance or the like in advance, it is possible to detect the bio-related molecules bound to the probe. The solution used for the binding reaction between the bio-related molecules and the probes contains, for example, bio-related molecules as well as a buffer solution prepared by adding SDS (sodium dodecyl sulfate) to citric acid-saline.

2. In addition, a second aspect of the present invention provides a carrier for bio-related molecule immobilization comprising: a water repellent resin substrate; an aminoalkylsilane layer formed on the resin substrate; and a polyvalent carboxylic acid layer formed on the aminoalkylsilane layer, wherein a carboxyl group of the polyvalent carboxylic acid layer is subjected to active esterification, and wherein the resin substrate is exposed after the formation of the aminoalkylsilane layer.

The substrate for the carrier used in the second aspect of the present invention is a water repellent resin substrate. In the second aspect of the present invention, a water repellent resin means an unhydrophilized resin or a resin which has been hydrophilized but its degree is low. Any type of unhydrophilized resin can be used in the present invention. The water repellent resin used in the second aspect of the present invention is preferably an unhydrophilized resin. However, even a resin substrate subjected to hydrophilization such as corona treatment or vacuum UV treatment can be used in the second aspect of the present invention as long as the degree of hydrophilization is low. Regardless of the presence or absence of hydrophilization, the water repellent resin of the second aspect of the present invention has a surface water contact angle of, for example, 66° or more, preferably 70° or more, more preferably 75° or more, and particularly preferably 80° or more.

It is common to hydrophilize the resin substrate for the purpose of efficiently forming an aminoalkylsilane layer on a resin substrate. However, the second aspect of the present invention uses a water repellent resin substrate which is not subjected to hydrophilization or which has been subjected to a low degree of hydrophilization to form a carrier with an exposed resin substrate after the formation of the aminoalkylsilane layer as further described later. Thus, it is possible to obtain a carrier for bio-related molecule immobilization with a good spot shape.

Although the type of resin is not particularly limited as long as the above conditions are satisfied, it is preferable to use a material having as low autofluorescence as possible because the detection of bio-related molecules such as nucleic acids is often carried out based on fluorescent substances bound to the bio-related molecules. Specifically, the types of resin include polyethylene, polypropylene, cyclic polyolefin, polyisobutylene, polyethylene terephthalate, unsaturated polyester, fluorine-containing resins, polyvinyl chloride, polyvinylidene chloride, polyvinyl acetate, polyvinyl alcohol, polyvinyl acetal, acrylic resins, polyacrylonitrile, polystyrene, acetal resins, polycarbonate, polyamide, phenolic resins, urea-formaldehyde resins, epoxy resins, melamine resins, styrene-acrylonitrile copolymer, acrylonitrile-butadiene styrene copolymer, and organic materials such as polyphenylene oxide and polysulfone, and a mixture resin of two or more kinds from these may be used. In addition, additional substances capable of improving the performance according to the desired purpose, such as improvement of detection sensitivity, may be added as appropriate, and a black pigment such as carbon black may be mixed, for example.

In the second aspect of the present invention, as the material for the resin substrate, it is preferable to use a polycarbonate and more preferable to use a polycarbonate containing a carbon black as a black pigment. The amount of the carbon black can be determined as appropriate by those skilled in the art, and the material used is one containing a carbon black in the resin in an amount of, for example, 0.1% by weight to 2% by weight, preferably 0.2% by weight to 1% by weight, and more preferably 0.3% by weight to 0.8% by weight.

In the carrier for bio-related molecule immobilization of the second aspect of the present invention, an aminoalkylsilane layer is formed on the resin substrate described above. For example, the aminoalkylsilane used is one whose alkyl group has 1 to 10 carbon atoms and preferably 2 to 5 carbon atoms, and specifically, the alkyl group includes methyl groups, ethyl groups, propyl groups, butyl groups, and pentyl groups. Among the above, a propyl group is particularly preferable in the second aspect of the present invention. In addition, the silane of the aminoalkylsilane may be substituted with one or more substituents. For example, it is possible to use one substituted with an alkoxy group (such as a methoxy group, an ethoxy group, a propoxy group, or a butoxy group) having 1 to 5 and preferably 2 to 4 carbon atoms. It is particularly preferable that the silane be substituted with three ethoxy groups. Specifically, the aminoalkylsilane includes 3-aminopropyltriethoxysilane, 3-aminopropyltrimethoxysilane, 3-aminopropyldiethoxymethylsilane, and 3-aminopropyldimethoxyethylsilane. In the second aspect of the present invention, 3-aminopropyltriethoxysilane is particularly preferable.

The aminoalkylsilane layer in the second aspect of the present invention is merely expressed as a "layer" for convenience based on the relative positional relationship of being formed on the resin substrate. The aminoalkylsilane layer may be formed on at least part of the surface of the substrate, and does not mean that the entire surface of the substrate is completely covered. That is, the carrier of the second aspect of the present invention is such that the resin substrate is exposed after the formation of the aminoalkylsilane layer. In the second aspect of the present invention, since the water repellent resin substrate is exposed after the formation of the aminoalkylsilane layer as described above, it is possible to eventually obtain a carrier for bio-related molecule immobilization with a good spot shape.

As described above, the phrase the resin substrate is exposed in the second aspect of the present invention means that the lower resin of the aminoalkylsilane layer is exposed on part of the surface of the carrier after the formation of the aminoalkylsilane layer. One of the methods of detecting resin exposure is a method of detecting the presence of substance components on the surface by surface analysis of the substrate after the formation of the aminoalkylsilane layer. Specifically, as an embodiment of the second aspect of the present invention, it is possible to make a judgment that the resin is exposed if a resin-derived peak is detected in surface analysis.

The above method of surface analysis can be selected as appropriate by those skilled in the art, and is preferably such a method that the detection depth is in a small range of about 1 to 10 nm. Examples thereof include X-ray photoelectron spectroscopy (XPS), Auger electron spectroscopy (AES), and time-of-flight secondary ion mass spectrometry (TOF-SIMS). Among the above, X-ray photoelectron spectroscopy (XPS) is preferable in the second aspect of the present invention. For example, consider the case of using a substrate of polycarbonate resin to measure its surface by X-ray photoelectron spectroscopy after the formation of the aminoalkylsilane layer. It is possible to make a judgment that the polycarbonate is exposed on the substrate surface after the formation of the aminoalkylsilane layer if a $\pi$-$\pi$ Shake-up peak is observed appearing in a range of a binding energy of 291.5 to 293.5 eV in the C1s spectrum, for example in the vicinity of 292.5 eV. Note that it is possible to make a judgment that a peak is present if the presence of a polycarbonate-derived peak is slightly observed in the C1s spectrum.

In addition, in the second aspect of the present invention, it is possible to make a judgment that the aminoalkylsilane layer does not completely cover the resin substrate and thus the resin substrate is exposed based on a predetermined controlled range of the content ratio of silicon obtained by measuring the substrate surface after the formation of the aminoalkylsilane layer by X-ray photoelectron spectroscopy. In the second aspect of the present invention, it is possible to make a judgment that the resin substrate is exposed if the content ratio of silicon is controlled at least in a range of 0.5 to 5.0 atomic %. The content ratio of silicon is more preferably 0.8 to 3.0 atomic % and further preferably 2.0 atomic %. In general, the higher the hydrophilicity (wettability) of the substrate surface, the easier the formation of the aminoalkylsilane layer, and the higher the content ratio of silicon. Therefore, particularly in the case of using a water repellent resin substrate (for example, a water contact angle of 66° or more), the amount of aminoalkylsilane introduced is suppressed as compared with a hydrophilic resin substrate, and the above-described content ratio of silicon is easily obtained. As a result, it is possible to obtain a carrier with an exposed resin substrate.

No particular limitation is imposed on the method of forming an aminoalkylsilane layer. For example, it is possible to form an aminoalkylsilane layer by immersing the substrate in a solution prepared by dissolving the aminoalkylsilane in various solvents. The types of solvent used can include alcohols such as methanol and ethanol. For the purpose of reducing the surface roughness of the substrate to suppress autofluorescence, it is preferable to use water as the solvent and immerse the substrate in an aqueous solution in which the aminoalkylsilane is sufficiently hydrolyzed.

The immersion time and the concentration of the solution of the aminoalkylsilane can be set as appropriate by those skilled in the art in consideration of the type of the specific compound used so as to obtain a predetermined surface analysis peak or silicon content ratio of the present invention as described above. For example, it is possible to use a solution of 0.1% by weight to 10% by weight and preferably 1% by weight to 8% by weight, and it is possible to set the immersion time to 15 minutes to 180 minutes and preferably 30 minutes to 150 minutes.

In the carrier for nucleic acid immobilization of the second aspect of the present invention, a polyvalent carboxylic acid layer is further formed on the aminoalkylsilane layer described above. When the polyvalent carboxylic acid layer is formed in this manner, carboxyl groups are introduced to the surface side of the carrier. No particular limitation is imposed on the type of the polyvalent carboxylic acid used in the second aspect of the present invention. For example, it is possible to use a homopolymer or a copolymer of a monomer having a carboxyl group such as polyacrylic acid, polymethacrylic acid, polymaleic acid, polyitaconic acid, and acrylic acid-methacrylic acid copolymers. When the carboxyl group of the polyvalent carboxylic acid forms an amide bond with the amino group of the aminoalkylsilane layer, the polyvalent carboxylic acid layer can be firmly bound on the aminoalkylsilane layer. Note that the polyvalent carboxylic acid layer may be formed on at least part of the surface of the underlying substrate and/or the aminoalkylsilane layer, and does not need to cover the entire surface of the substrate and/or the aminoalkylsilane layer. Since the polyvalent carboxylic acid layer is formed on the aminoalkylsilane layer due to the amide bond between the carboxyl groups and the amino groups as described above, it is assumed that the resin substrate exposed after the formation of the aminoalkylsilane layer is still exposed after the formation of the polyvalent carboxylic acid layer.

No particular limitation is imposed on the method of forming a polyvalent carboxylic acid layer. The method includes a method of immersing the substrate having an aminoalkylsilane layer formed thereon in a solution of the polyvalent carboxylic acid. The solvent used for the solution of the polyvalent carboxylic acid can be selected as appropriate by those skilled in the art, and it is possible to use water and various types of organic solvents including alcohols such as methanol and ethanol. In the second aspect of the present invention, it is preferable to use an aqueous solution.

The immersion time, the concentration, and the molecular weight of the solution of the polyvalent carboxylic acid layer can be set as appropriate by those skilled in the art. For example, the molecular weight selected is 25,000 to 1,000,000, preferably 50,000 to 500,000, and particularly preferably 100,000 to 200,000, the concentration selected is 0.1% by weight to 10% by weight, preferably 0.5% by weight to 10% by weight, and particularly preferably 1.0% by weight to 5.0% by weight, and the immersion time selected is 1 minutes to 60 minutes, preferably 5 minutes to 30 minutes, and particularly preferably 10 minutes to 20 minutes.

In the carrier for nucleic acid immobilization of the second aspect of the present invention, the carboxyl groups of the polyvalent carboxylic acid layer formed as described above are subjected to active esterification. When the carboxyl groups are subjected to active esterification to form active ester groups, it is possible to stably immobilize nucleic acids at the time of eventually spotting a solution of nucleic acids as a carrier for nucleic acid immobilization. As regards the type of active ester group and a method of forming the same, there is no particular limitation thereon and those skilled in the art can appropriately select ones suitable for the application as a carrier for nucleic acid immobilization. The active ester group includes nitrophenyl groups, N-hydroxysuccinimide groups, N-hydroxynorbornene-2,3-dicarboximide groups, succinimide groups, and phthalimide groups. In the second aspect of the present invention, N-hydroxysuccinimide groups are preferable. The method of forming active ester groups includes active esterification of the carboxyl groups of the polyvalent carboxylic acid layer by immersion in a solution prepared by dissolving a dehydration condensation agent such as 1-ethyl-3-(3-dimethylaminopropyl)carbodiimide hydrochloride and any type of electrophilic group introducing agent corresponding to the active ester group as described above (such as N-hydroxysuccinimide) in a buffer solution.

The carrier for bio-related molecule immobilization of the second aspect of the present invention obtained as described above can immobilize bio-related molecules on its surface. The bio-related molecules in the second aspect of the present invention are preferably nucleic acids. A nucleic acid-containing solution is spotted on a carrier for bio-related molecule immobilization, followed by washing of the unreacted nucleic acid solution not bound on the carrier. Thus, it is possible to obtain a carrier with immobilized nucleic acids. The method of spotting a nucleic acid-containing solution on the carrier includes, but is not particularly limited to, a spotting method including bringing a pin holding a nucleic acid-containing solution into contact with the carrier and a method of spraying by ink-jet a nucleic acid-containing solution on the carrier. It is possible to carry out spotting using any apparatus, method, and the like known to those skilled in the art.

The nucleic acid immobilization carrier prepared as described above can be used for detecting the presence of target nucleic acids in the test sample. For example, consider the case of using DNA as a nucleic acid. DNA is extracted from the test sample and amplified, which is hybridized with nucleic acids on a nucleic acid immobilization carrier (such as a DNA chip or a microarray) for detection. This makes it possible to confirm the presence or absence of specific microbial contamination in the test sample. The method of extracting DNA includes the phenol extraction method, the phenol-chloroform extraction method, the alkali dissolution method, and the boiling method. Examples also include a method of extracting DNA using a commercially available DNA extracting reagent or a nucleic acid automatic extraction apparatus.

The target region of the extracted DNA is amplified by a nucleic acid amplification method, if necessary. The target region is a region of chromosomal DNA which can be amplified by the nucleic acid amplification method, and can be set as appropriate depending on the purpose without particular limitation as long as it is possible to detect the detection target microorganism. For example, when the test sample contains cells different in type from the detection target microorganism, the target region preferably has a sequence specific to the detection target microorganism, or may have a sequence common to two or more types of microorganisms depending on the purpose. The nucleic acid amplification method includes the PCR method (polymerase chain reaction), the SDA method (strand displacement amplification), the LCR method (ligase chain reaction), the LAMP method (loop-mediated isothermal amplification), and the ICAN method (isothermal and chimeric primer-initiated amplification of nucleic acids). Among these, it is preferable to use the PCR method. For example, the length of a target region amplified by the PCR method is usually 80 to 1000 bases and preferably 100 to 500 bases.

The amplified DNA is detected with the nucleic acid immobilization carrier of the second aspect of the present invention. The nucleic acids (probes) immobilized on the carrier are detectors which enable detection by binding only to the target bio-related molecules in the case where various bio-related molecules such as specific genes and proteins are coexistent, and it is thus difficult to make a distinguishment from one another and to make a direct selection. For example, consider the case of detecting the nucleic acid of a specific microorganism as a bio-related molecule. The probes used are DNA fragments having a sequence complementary to the base sequence possessed by the nucleic acid of this microorganism, and hybridization with the nucleic acid is carried out. Usually, DNAs of 1 to 200 bases and preferably 10 to 150 bases are immobilized on the probes. Either single stranded or double stranded DNA can be immobilized. In addition, when the target bio-related molecules are labeled with a fluorescent substance or the like in advance, it is possible to detect the bio-related molecules bound to the probe. The solution used for the binding reaction between the bio-related molecules and the probes contains, for example, bio-related molecules as well as a buffer solution prepared by adding SDS (sodium dodecyl sulfate) to citric acid-saline.

Hereinafter, the aspects of the present invention are described in more detail based on Examples.

EXAMPLES

1. Examples for First Aspect of Present Invention

Preparation of Surface-Treated Substrate

A polycarbonate substrate containing a carbon black (manufactured by Shiraishi Kogyo Kaisha, Ltd.) was immersed in a 5-wt % aqueous solution of 3-aminopropyl-triethoxysilane (AS solution) for 30 to 120 minutes to introduce amino groups. This substrate, into which amino groups were introduced, was immersed in an aqueous solution of polyacrylic acid (PA solution) having a molecular weight of about 150,000, then washed with pure water, and immersed for 10 minutes in an activation solution prepared by dissolving 0.1 M of 1-ethyl-3-(3-dimethylaminopropyl) carbodiimide hydrochloride and 0.05 M of N-hydroxysuccinimide in a 0.1 M phosphate buffer solution (pH 6.8), followed by activation of carboxyl groups to prepare a surface-treated substrate. The above procedures were followed to prepare a substrate with a different amount of carboxyl group introduced by changing the concentration of the aqueous solution of polyacrylic acid used for the immersion in a range of 0.5% to 10%, as presented in the table provided later. In addition, the substrate surface after the polyacrylic acid treatment was measured with an X-ray photoelectron spectrometer (K-Alpha XPS system manufactured by Thermo Fisher Scientific) to obtain a C1s spectrum. Measurement was conducted on the intensity of the peak derived from hydrocarbons and obtained in the vicinity of 284.7 eV (C—C peak intensity) and the intensity of the peak derived from carboxyl groups and obtained in the vicinity of 288.4 eV (COO peak intensity). Then, the ratio between them was calculated.

FIG. 1 illustrates a C1s spectrum of XPS surface analysis on a substrate after polyacrylic acid treatment of Example 1-4. The peak detected in the vicinity of 288.4 eV is the C—C peak considered to be mainly derived from the polycarbonate substrate, and the peak detected in the vicinity of 284.7 eV is the COO peak considered to be derived from the carboxyl groups of the polyvalent carboxylic acid layer.

Preparation of DNA Immobilizing Substrate

A DNA probe solution prepared to 10 mM using a microarray preparation apparatus (MARKS-I manufactured by Koden Industry Co., Ltd.) was spotted on the surface-treated substrate. The substrate on which the DNA probe was spotted was heated in an oven at 80° C. for 1 hour, and then the spot diameter was measured by observation using a stereomicroscope (Leica EZ4D manufactured by Leica Microsystems, Inc.). The substrate was washed with 2×SSC/0.2% SDS at room temperature for 10 minutes and at 60° C. for 10 minutes to prepare a DNA immobilization substrate.

Preparation of Mold PCR Product and Evaluation of Detection Sensitivity

*Aspergillus fumigatus* was cultured on a plate medium, and DNA was extracted from the obtained colonies. This was prepared at a concentration of 50 pg/µL as a template DNA, followed by amplification by PCR to obtain a PCR product for evaluation of detection sensitivity.

| Composition of PCR Reaction Solution | |
|---|---|
| dH$_2$O | 8.6 |
| 5x Ampdirect ® G/C | 4.0 |
| 5x Amp addition-4 | 4.0 |
| dNTPs | 1.0 |
| Primer | 1.0 |
| Cy5-dCTP | 0.2 |
| NovaTaq HS DNA polymerase | 0.2 |
| Template DNA(50 pg/µL) | 1.0 |
| Total (µL) | 20.0 |

| PCR Conditions | | |
|---|---|---|
| 95° C. | 10 Minutes | |
| 95° C. | 30 Seconds | 40 Cycles |
| 56° C. | 30 Seconds | |
| 72° C. | 60 Seconds | |
| 72° C. | 10 Minutes | |

Detection

A hybridization buffer in an amount of 2 µL and the PCR product in an amount of 4 µL were mixed to come into contact with the surface of the prepared DNA immobilization substrate, followed by reaction at 45° C. for 60 minutes. After the reaction, the substrate was subjected to sway washing with a 0.5×SSC/0.2% SDS solution and then with a 0.5×SSC solution twice for 50 cycles each. A cover glass was placed thereon, and a DNA chip detection apparatus (GENOGATE Reader manufactured by Toyo Kohan Co., Ltd.) was used to obtain a fluorescence detection image. The S/N ratio was calculated from the fluorescence intensity value and the background value obtained from each of the spots on the detection image.

The table below presents the calculated values of the C—C peak intensity and the COO peak intensity and their peak intensity ratios regarding the carrier for nucleic acid immobilization prepared as described above (before ester activation) as well as the S/N ratios and the spot diameters measured after DNA immobilization.

TABLE 1

| | Comparative Example 1-1 | Example 1-1 | Example 1-2 | Example 1-3 | Example 1-4 | Example 1-5 | Example 1-6 | Example 1-7 |
|---|---|---|---|---|---|---|---|---|
| Concentration of AS Solution-Immersion Time | 5%-60 min | 5%-120 min | 5%-30 min | 5%-60 min | 5%-120 min | 5%-30 min | 5%-60 min | 5%-120 min |
| Concentration of PA Solution-Immersion Time | 0.5%-10 min | | | 1%-10 min | | | 2%-10 min | |

TABLE 1-continued

| C—C Peak Intensity | 3378.6 | 3330.19 | 3350.95 | 3372.51 | 3308.88 | 3298.2 | 3282.56 | 3281.64 |
|---|---|---|---|---|---|---|---|---|
| COO Peak Intensity | 192.89 | 212.93 | 234.1 | 225.48 | 263.88 | 312.91 | 289.07 | 308.9 |
| COO/C—C Peak Intensity Ratio | 0.057 | 0.064 | 0.070 | 0.067 | 0.080 | 0.095 | 0.088 | 0.094 |
| S/N(Af1-1) | 5.6 | 6.8 | 7.5 | 7.3 | 6.6 | 7.8 | 7.7 | 8.3 |
| Spot Diameter (um) | 148 | 148 | 146 | 139 | 145 | 159 | 162 | 154 |

| | Example 1-8 | Example 1-9 | Example 1-10 | Comparative Example 1-2 | Comparative Example 1-3 |
|---|---|---|---|---|---|
| Concentration of AS Solution-Immersion Time | 5%-30 min | 5%-60 min | 5%-120 min | 5%-30 min | 5%-120 min |
| Concentration of PA Solution-Immersion Time | | 5%-10 min | | 10%-10 min | |
| C—C Peak Intensity | 3312.32 | 3269.62 | 3194.74 | 3205.17 | 3178.55 |
| COO Peak Intensity | 352.77 | 393.31 | 377.98 | 466.34 | 444.99 |
| COO/C—C Peak Intensity Ratio | 0.107 | 0.12 | 0.118 | 0.145 | 0.140 |
| S/N(Af1-1) | 7.8 | 7.3 | 7.9 | 5.0 | 4.8 |
| Spot Diameter (um) | 169 | 176 | 174 | 178 | 191 |

The mold PCR product was hybridized to evaluate the detection sensitivity of the DNA immobilization substrate. The above results were such that it was possible to obtain a DNA chip with high detection sensitivity while keeping the spot diameter small when a nucleic acid solution was spotted on a carrier in which the COO/C—C peak intensity ratio of the substrate surface after the formation of the polyvalent carboxylic acid layer was in a range of 0.064 to 0.12.

2. Experimental Examples for Second Aspect of Present Invention

Experimental Example 2-1

Figure 2:
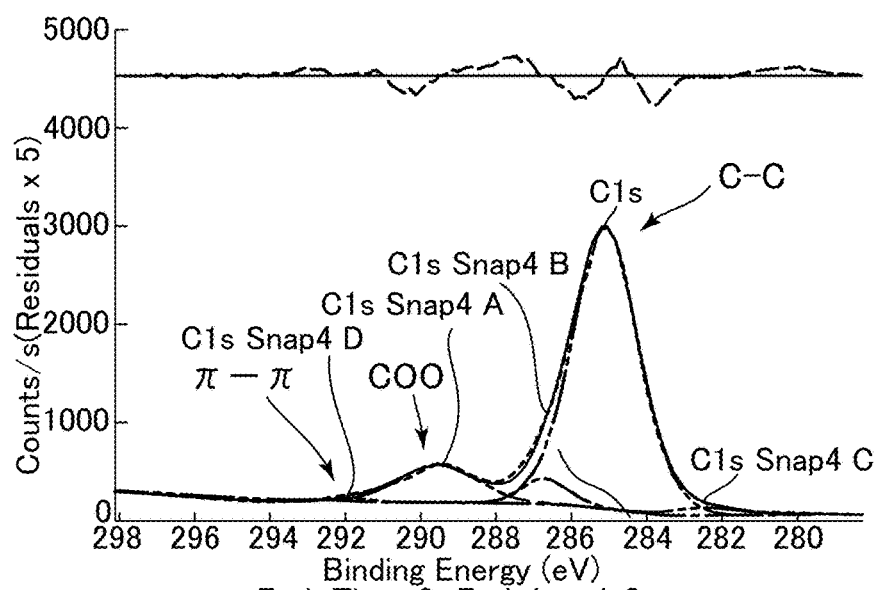
FIG. 2 illustrates C1s spectrum charts for Experimental Examples 2-1, 2-10, and 2-16, obtained in XPS analysis on substrate surfaces after polyacrylic acid adsorption.
Figure 2:
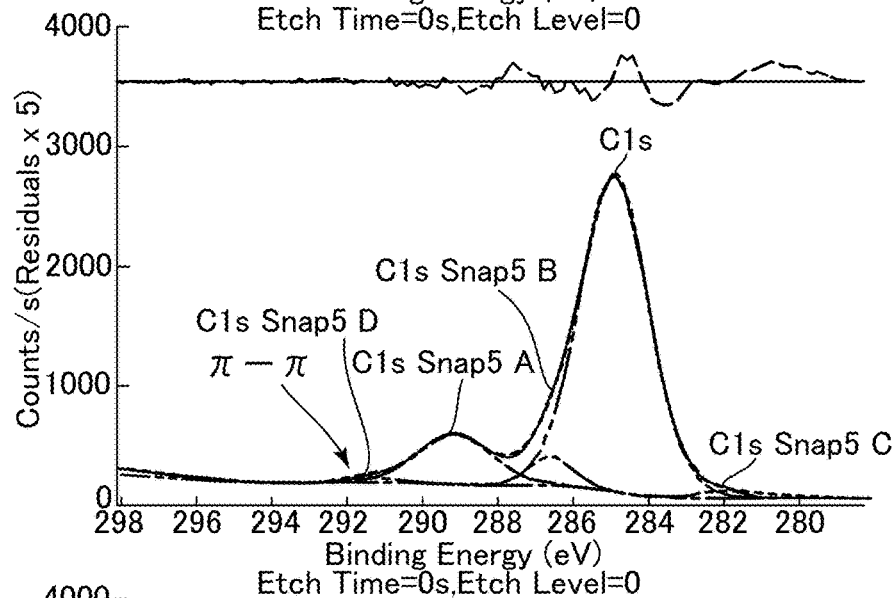
Figure 2:
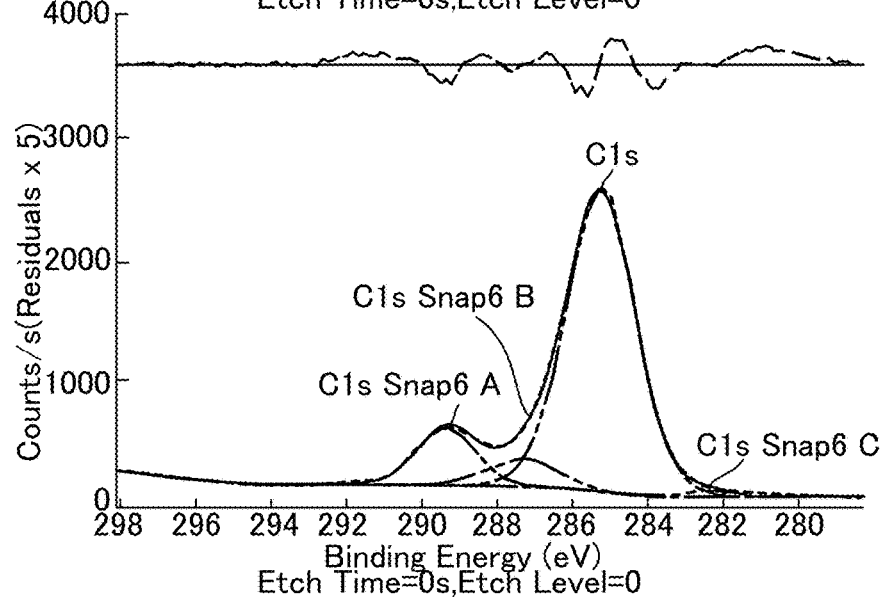
Figure 3:
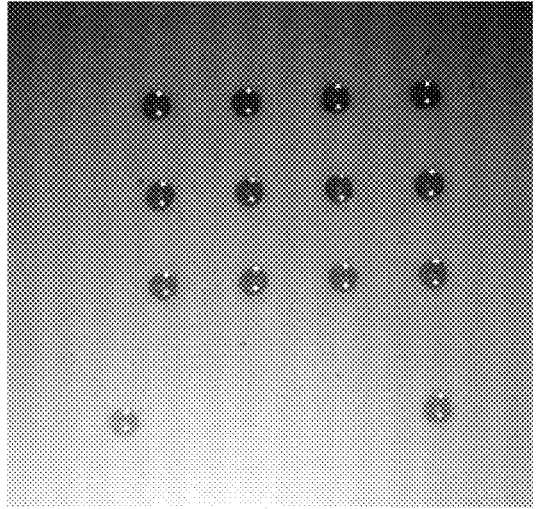
FIG. 3 illustrates actual spot observation images for Experimental Examples 2-1, and 2-10, and 2-16.
Figure 3:
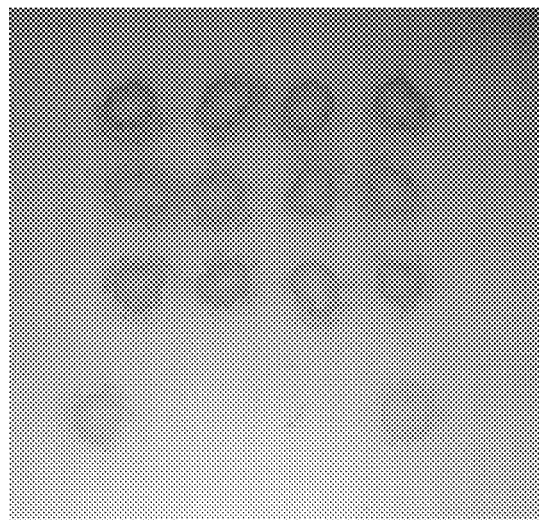
Figure 3:
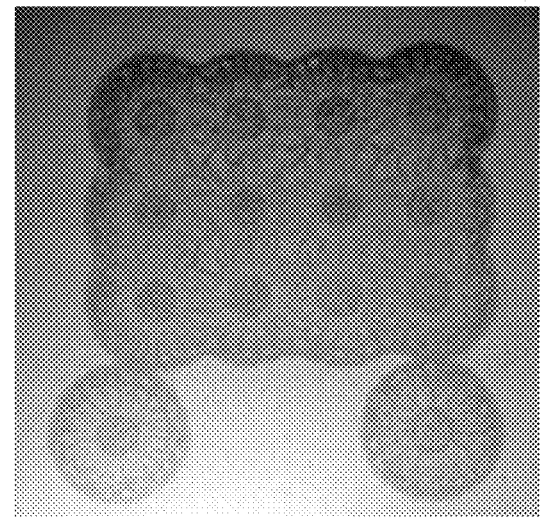
Figure 4:
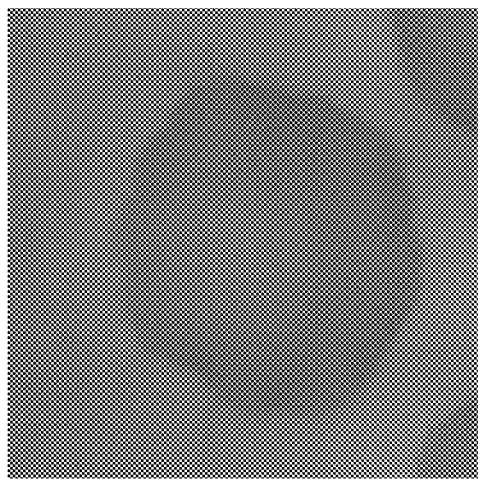
FIG. 4 illustrates actual spot observation images for Experimental Examples 2-11 to 2-15.
Figure 4:
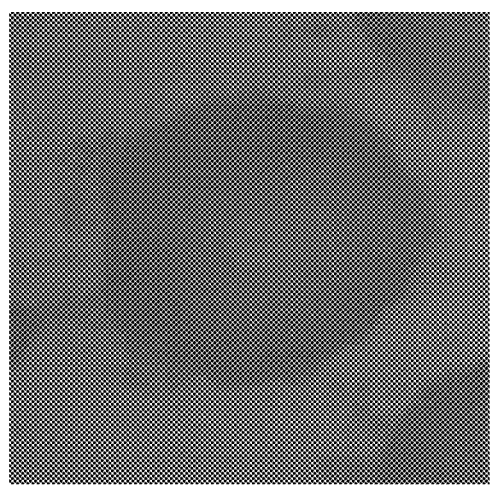
Figure 4:
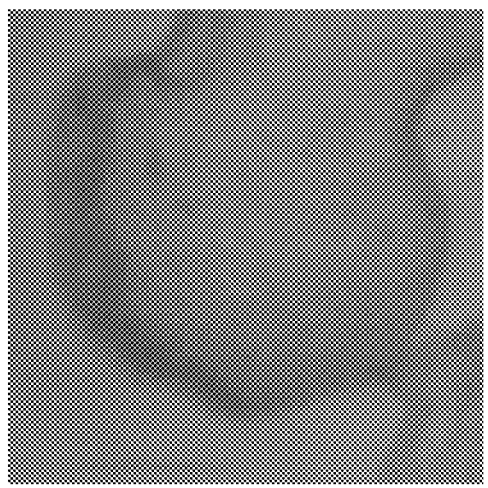
Figure 4:
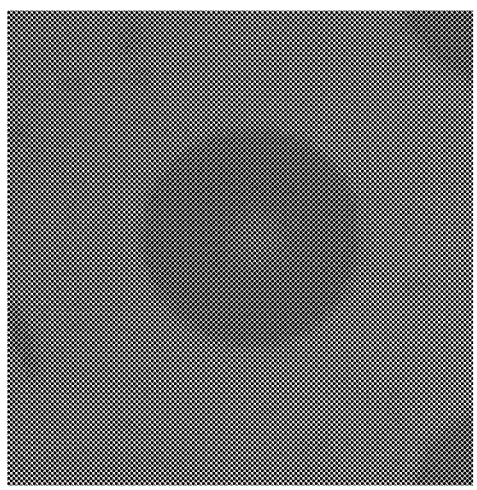
Figure 4:
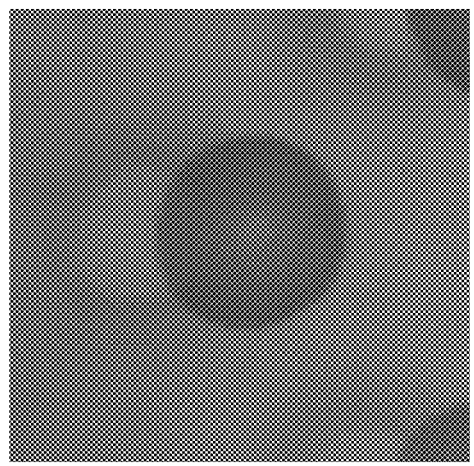

A polycarbonate substrate containing a carbon black (manufactured by Shiraishi Kogyo Kaisha, Ltd., hereinafter the black PC substrate) was prepared, and a contact angle meter (DropMaster 700 manufactured by Kyowa Interface Science, Inc.) was used to measure the water contact angle. Next, the black PC substrate was immersed in a 5-wt % aqueous solution of 3-aminopropyltriethoxysilane for 2 hours, then taken out therefrom, washed with pure water, and then dried at 70° C. for 2 hours. This substrate was measured with an X-ray photoelectron spectrometer (K-Alpha XPS system manufactured by Thermo Fisher Scientific) to confirm the content ratio of Si. Next, a portion not subjected to ESCA measurement was immersed in a 1% aqueous solution of polyacrylic acid for 10 minutes, then taken out therefrom, washed with pure water, and then dried at 80° C. for 2 hours. This substrate was measured with an X-ray photoelectron spectrometer to obtain a C1s spectrum. FIG. 2 illustrates charts after peak separation.

Next, a portion not subjected to ESCA measurement was activated by immersion for 10 minutes in an activation solution prepared by dissolving 0.1 M of 1-[3-(dimethylamino)propyl]-3-ethylcarbodiimide hydrochloride and 0.1 M of N-hydroxysuccinimide in 200 ml of a 0.1 M phosphate buffer solution (pH 6.8). A 30% solution of PEG 300 containing oligo DNA (10 μM) was spotted on the obtained solid support, followed by heating at 80° C. for 1 hour to photograph the spot shape with a stereomicroscope (Leica EZ4D manufactured by Leica Microsystems, Inc.). In addition, the diameter of each spot was measured on image processing software based on the spot image photographed using a stereomicroscope with a built-in digital camera, and the spot diameter was calculated by averaging the diameters in the X-axis direction and the Y-axis direction.

Experimental Example 2-2

A substrate was prepared in the same manner as that of Experimental Example 2-1 except that the immersion time in the aqueous solution of 3-aminopropyltriethoxysilane was changed to 30 minutes.

Experimental Example 2-3

A substrate was prepared in the same manner as that of Experimental Example 2-1 except that the concentration of the aqueous solution of 3-aminopropyltriethoxysilane was changed to 1% and the immersion time was changed to 30 minutes.

Experimental Example 2-4

A substrate was prepared in the same manner as that of Experimental Example 2-1 except that the concentration of the aqueous solution of 3-aminopropyltriethoxysilane was changed to 0.1% and the immersion time was changed to 30 minutes.

Experimental Example 2-5

A substrate was prepared in the same manner as that of Experimental Example 2-1 except that the black PC was changed to a carbon black-free PC.

Experimental Example 2-6

A substrate was prepared in the same manner as that of Experimental Example 2-1 except that the black PC was changed to polybutylene terephthalate (PBT).

Experimental Example 2-7

A substrate was prepared in the same manner as that of Experimental Example 2-1 except that the black PC was changed to polymethyl methacrylate (PMMA).

Experimental Example 2-8

A substrate was prepared in the same manner as that of Experimental Example 2-1 except that the black PC was changed to polypropylene (PP).

Experimental Example 2-9

A substrate was prepared in the same manner as that of Experimental Example 2-1 except that the black PC was changed to polymethylpentene (PMP).

Experimental Example 2-10

A substrate was prepared in the same manner as that of Experimental Example 2-1 except that the black PC was changed to a black PC having hydrophilic groups introduced on its surface by corona irradiation.

Experimental Example 2-11

A substrate was prepared in the same manner as that of Experimental Example 2-1 except that the black PC was changed to a carbon black-free PC having hydrophilic groups introduced on its surface by corona irradiation.

Experimental Example 2-12

A substrate was prepared in the same manner as that of Experimental Example 2-1 except that the black PC was changed to PBT having hydrophilic groups introduced on its surface by corona irradiation.

Experimental Example 2-13

A substrate was prepared in the same manner as that of Experimental Example 2-1 except that the black PC was changed to PMMA having hydrophilic groups introduced on its surface by corona irradiation.

Experimental Example 2-14

A substrate was prepared in the same manner as that of Experimental Example 2-1 except that the black PC was changed to PP having hydrophilic groups introduced on its surface by corona irradiation.

Experimental Example 2-15

A substrate was prepared in the same manner as that of Experimental Example 2-1 except that the black PC was changed to PMP having hydrophilic groups introduced on its surface by corona irradiation.

Experimental Example 2-16

A substrate was prepared in the same manner as that of Experimental Example 2-1 except that the black PC was changed to a black PC having hydrophilic groups introduced on its surface by vacuum UV irradiation.

Regarding Experimental Examples 2-1 to 2-13, Table 2 presents the resin substrates used, hydrophilization performed, water contact angles before the surface treatment, content ratios of Si after the formation of the aminoalkylsilane layer, presence or absence of resin peak detection by X-ray photoelectron spectroscopy, spot shapes, and spot diameters.

TABLE 2

| | Substrate | Hydrophilization Treatment | Water Contact Angle Before Surface Treatment (°) | Si Content Ratio (at %) | Resin Peak Detection | Spot Shape | Spot Diameter (μm) |
|---|---|---|---|---|---|---|---|
| Experimental Example 2-1 | Black PC | x | 82.7 | 1.89 | ○ | ○ (Good) | 168 |
| Experimental Example 2-2 | Black PC | x | 82.7 | 1.46 | — | ○ (Good) | — |
| Experimental Example 2-3 | Black PC | x | 82.7 | 1.08 | — | ○ (Good) | — |
| Experimental Example 2-4 | Black PC | x | 82.7 | 0.64 | — | ○ (Good) | — |
| Experimental Example 2-5 | PC | x | 79.3 | 2.22 | — | ○ (Good) | — |
| Experimental Example 2-6 | PBT | x | 76.9 | 1.52 | — | ○ (Good) | — |
| Experimental Example 2-7 | PMMA | x | 72.8 | 1.33 | — | ○ (Good) | — |
| Experimental Example 2-8 | PP | x | 98.5 | 1.23 | — | ○ (Good) | — |
| Experimental Example 2-9 | PMP | x | 106.6 | 0.81 | — | ○ (Good) | — |
| Experimental Example 2-10 | Black PC | Corona | 65.2 | 2.66 | ○ | Δ (Partial Blurring) | 382 |
| Experimental Example 2-11 | PC | Corona | 49.1 | 3.11 | — | Δ (Partial Blurring) | 375 |

TABLE 2-continued

| | Substrate | Hydrophilization Treatment | Water Contact Angle Before Surface Treatment (°) | Si Content Ratio (at %) | Resin Peak Detection | Spot Shape | Spot Diameter (μm) |
|---|---|---|---|---|---|---|---|
| Experimental Example 2-12 | PBT | Corona | 46.6 | 1.80 | — | Δ (Partial Blurring) | 378 |
| Experimental Example 2-13 | PMMA | Corona | 55.0 | 1.42 | — | x (Spot Fusion) | 445 |
| Experimental Example 2-14 | PP | Corona | 66.1 | 1.57 | — | ○ (Good) | 231 |
| Experimental Example 2-15 | PMP | Corona | 72.8 | 1.56 | — | ○ (Good) | 220 |
| Experimental Example 2-16 | Black PC | Vacuum UV | 46.5 | 6.00 | x | xx (Treatment Film Broken) | 871 |

* "—": Not measured.

As presented in Experimental Examples 2-1, 2-10, and 2-16 of Table 2, the contact angle decreased due to hydrophilization, and the amount of aminoalkylsilane layer introduced (content ratio of Si) increased accordingly. Good spots were obtained in Experimental Example 2-1, whereas the spots blurred in Experimental Example 2-10 and the spot form in Experimental Example 2-16 was as if the treatment film was broken.

In addition, as illustrated by the C1s spectrum charts of FIG. 2, Experimental Example 2-1 and Experimental Example 2-10 observed a PC-derived π-π Shake-up peak appearing in the vicinity of a binding energy of 292.5 eV in X-ray photoelectron spectroscopy after the formation of the aminoalkylsilane layer. It is presumed from the above facts that the aminoalkylsilane layer was thinly formed and the PC surface was exposed in the substrate prepared under these experimental conditions. On the other hand, Experimental Example 2-16 was unable to observe a π-π Shake-up peak. For this reason, it is presumed that, in Experimental Example 2-16, the substrate surface was covered with a thick aminoalkylsilane layer and the PC surface was not exposed.

It is understood from these facts that the aminoalkylsilane layer was thinly formed in Experimental Example 2-1 so that the water repellent substrate was exposed, in which state it was possible to obtain a good spot shape. In addition, it is understood that the hydrophilized substrate was exposed in Experimental Example 2-10, in which state it was possible to obtain good spots but partial blurring occurred. Moreover, it is understood that the substrate in Experimental Example 2-16 was covered with the aminoalkylsilane layer and thus was not exposed, in which state the spot shape was poor.

It is understood from the above facts that the spot shape can be stabilized by controlling the exposure state of the substrate after the formation of the aminoalkylsilane layer and the wettability of the surface of the exposed resin substrate.

In addition, as presented by Experimental Examples 2-2 to 2-4 of Table 2, it is possible to prepare a substrate which has exposed resin and has a further thinly-formed aminoalkylsilane layer by changing the immersion time and the concentration of the aqueous solution of 3-aminopropyltriethoxysilane, and it is understood that any of them has a good spot shape and makes it possible to stabilize the spot shape in the same manner as that of Experimental Example 2-1 even in the case of a substrate having a Si content ratio of about 0.64 atomic %.

Furthermore, as presented by Experimental Examples 2-5 to 2-9 and 2-11 to 2-15 of Table 2, the water contact angles of the unhydrophilized samples were 72.8 to 106.6° and their spot shapes were good. On the other hand, in the hydrophilized samples, the water contact angles decreased to 46.6 to 72.8° and their Si content ratios were 1.42 to 3.11 atomic %. It is presumed that, with a content ratio in this range, a thin aminoalkylsilane layer is formed and the surface of the resin substrate is exposed. The spot shape was good in the case of using a substrate having a water contact angle of 66.1° or more (Experimental Examples 2-14 and 2-15), and blurring occurred in the case of using a substrate having a water contact angle smaller than the above (Experimental Examples 2-11 to 2-13).

The following is understood from what has been described above. The wettability of the surface of an exposed resin substrate greatly affects the spot shape, and it is possible to obtain good spots without blurring in the case of a substrate which has a thinly formed aminoalkylsilane layer and thus is presumed to have an exposed resin surface, in which the water contact angle of the exposed resin surface is 66.1° or more.

What is claimed is:

1. A carrier for bio-related molecule immobilization comprising:
    a water repellent resin substrate, wherein a water contact angle on a surface of the water repellent resin substrate is at least 66° before surface treatment;
    an aminoalkylsilane layer formed on the surface of the water repellent resin substrate; and
    a polyvalent carboxylic acid layer formed on the aminoalkylsilane layer,
    wherein a carboxyl group of the polyvalent carboxylic acid layer is subjected to active esterification, wherein the water repellent resin substrate is exposed after the formation of the aminoalkylsilane layer, and wherein a content ratio of silicon in the substrate surface after the formation of the aminoalkylsilane layer is from 0.5 atomic % to 3.11 atomic %.

2. The carrier for bio-related molecule immobilization according to claim 1, wherein a resin-derived peak is detected in surface analysis of the water repellent resin substrate after the formation of the aminoalkylsilane layer.

3. The carrier for bio-related molecule immobilization according to claim 1, wherein the water repellent resin substrate is a polycarbonate, and wherein a π-π Shake-up peak is detected in a C1s spectrum by X-ray photoelectron spectroscopy on the substrate surface after the formation of the aminoalkylsilane layer.

4. The carrier for bio-related molecule immobilization according to claim 1, wherein the water repellent resin substrate is a polycarbonate containing a black pigment.

5. A method of producing the carrier of claim 1 for bio-related molecule immobilization, the method comprising:
  forming an aminoalkylsilane layer on a water repellent resin substrate;
  forming a polyvalent carboxylic acid layer on the aminoalkylsilane layer; and
  subjecting a carboxyl group of the polyvalent carboxylic acid layer to active esterification,
  wherein the step of forming an aminoalkylsilane layer is conducted under a condition that the water repellent resin substrate is exposed after the formation of the aminoalkylsilane layer.

* * * * *